United States Patent [19]

Beasley et al.

[11] Patent Number: 4,906,851

[45] Date of Patent: Mar. 6, 1990

[54] U.V. TOOTHBRUSH STERILIZER AND TOOTHBRUSH HOLDER

[76] Inventors: Gary R. Beasley, 89612 Unit E, Boley, Okla. 74829; George Spector, 233 Broadway Rm 3815, New York, N.Y. 10007

[21] Appl. No.: 245,443

[22] Filed: Sep. 16, 1988

[51] Int. Cl.$^4$ .............................................. A61L 3/00
[52] U.S. Cl. ................................ 250/455.1; 250/498.1
[58] Field of Search ............. 250/455.1, 498.1, 504 R

[56] References Cited

U.S. PATENT DOCUMENTS

| | | | |
|---|---|---|---|
| 2,145,196 | 1/1939 | Biggs | 250/455.1 |
| 2,146,688 | 2/1939 | Selig | 250/455.1 |
| 3,906,236 | 9/1975 | Callahan | 250/455.1 |
| 4,803,364 | 2/1989 | Ritter | 250/455.1 |

Primary Examiner—Janice A. Howell

[57] ABSTRACT

A device for sterilizing and storing toothbrushes is provided which includes a container for holding the toothbrushes therein whereby current to a ultraviolet ray lamp that supplies an application of germicidal radiation to bristles of toothbrushes stored therein can be automatically deenergized when the container is in an opened position at a predetermined distance.

2 Claims, 1 Drawing Sheet

U.V. TOOTHBRUSH STERILIZER AND TOOTHBRUSH HOLDER

BACKGROUND OF THE INVENTION

The instant invention relates generally to sterilizers and more specifically it relates to a device for sterilizing and storing toothbrushes.

Numerous sterilizers have been provided in prior art that are adapted to radiate ultraviolet rays to destroy bacteria and fungi on various items placed thereion. For example, U.S. Pats. No. 2,554,156; 2,587,131 and 2,822,476 all are illustrative of such prior art. While these units may be suitable for the particular purpose to which they address, they would not be as suitable for the purposes of the present invention as heretofore described.

SUMMARY OF THE INVENTION

A primary object of the present invention is to provide a device for sterilizing and storing toothbrushes that will overcome the shortcomings of the prior art devices.

Another object is to provide a device for sterilizing and storing toothbrushes that can supply an application of germicidal radiation to bristles of toothbrushes stored therein.

An additional object is to provide a device for sterilizing and storing toothbrushes that includes a container for holding the toothbrushes therein whereby current to an ultraviolet ray lamp can be automatically deenergized when opening the container a predetermined distance.

A further object is to provide a device for sterilizing and storing toothbrushes that is simple and easy to use.

A still further object is to provide a device for sterilizing and storing toothbrushes that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
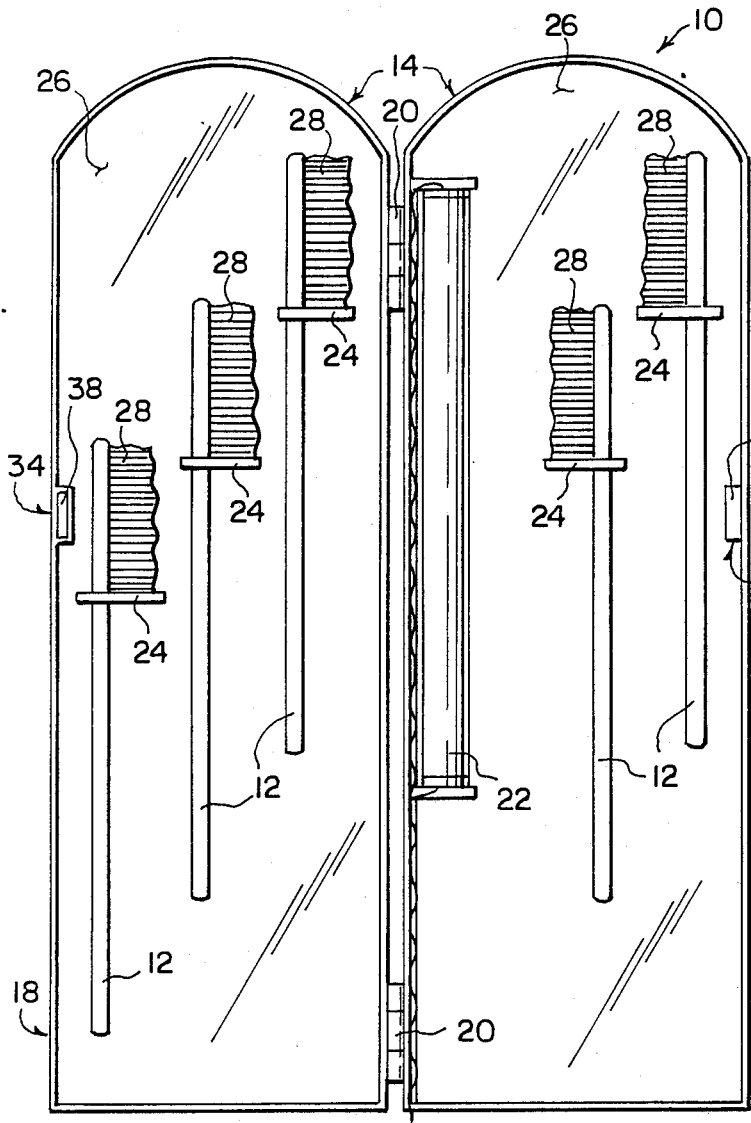
FIG. 1 is a front view of the invention in an opened position.

Turning now descriptively to the drawings, in which similar reference characters denote similar elements throughout the several views the figures illustrate a device 10 for sterilizing and storing toothbrushes 12 consisting of a container 14 having a first half segment 16 and a second half segment 18 hinged together at 20 so that in one instance the segments can be in an opened position and in another instance the segments can be in closed position. A lamp 22 is disposded within the first half segment 16 for radiating ultraviolet rays. Holders 24 are provided for supporting the toothbrushes 12, in which the holders 24 are spaced apart and affixed to interior of the first half segment 16 and the second half segment 18. Reflecting surfaces 26 are on the interior of the first half segment 16 and the second half segment 18 for directing rays from the lamp 22 over bristels 28 of the toothbrushes 12. An electrical connection 30, such as a power cord, goes from the lamp 22 to a power source 32, such as a battery or house lighting circuit. A magnetic fastener 34 is for removably securing the first half segment 16 to the second half segment 18 in the closed position. A mechanism 36 is for automatically denerginzing the lamp 22 when the first half segment 16 and the second half segment 18 are in the opened position at a predetermined distance.

The magnetic fastener 34 includes a magnetizable member 38 affixed to the second half segment 18 of the container 14. A magnetic member 40 is affixed to the first half segment 16 of the container 14 so that when the segments are in the closed position the magnetic member 40 and the magnetizable member 38 will make contact with each other.

Figure 2:
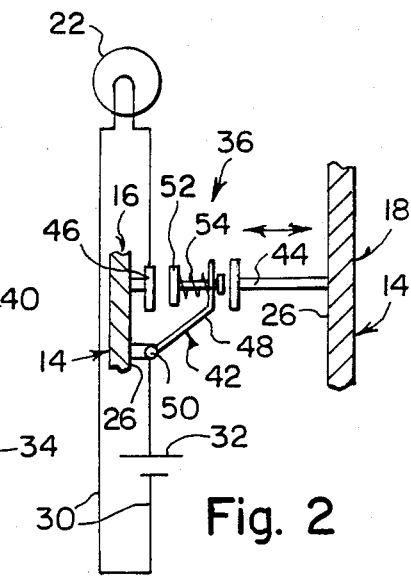
FIG. 2 is a schematic diagram of the electrical circuit of the switch.

As shown in FIG. 2, the mechanism 36 includes a switch 42 in the electrical connection 30 and is disposed onto the first half segment 16 of the container 14 for controlling energization of the lamp 22. An actuator 44 is attached to the second half segment 18 of the container 14 and is controlled by movement thereof for operating the switch 42 to energize the lamp 22 when the second half segment 18 is in the closed position and to deenergize the lamp 22 when the second half segment 18 is in the opened position.

The switch 42 includes a stationary contact 46 mounted to the interior 26 of the first half segment 16 of the container 14. A moveable arm 48 is pivotly mounted at 50 to the interior 26 of the first half segment 16 while an adjustable contact 52 is disposed onto the moveable arm 48. A spring 54 is disosed between the adjustable contact 52 and the moveable arm 48 to bias the adjustable contact 52. In one instance the adjustable contact 52 will permit the second half segment 16 of the container 14 to go into the closed position before the lamp 22 is energized and in another instance permit the second half segment 16 to go into the closed position after the lamp 22 is energized.

Figure 3:
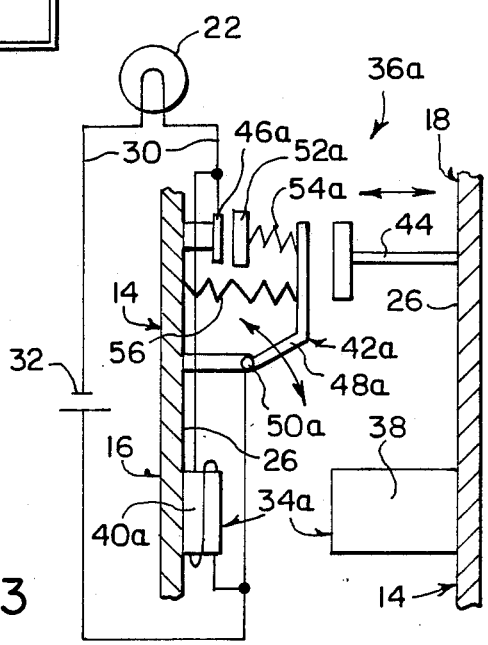
FIG. 3 is a schematic diagram of the electrical circuit of another form of the switch.

FIG. 3 shows a modified mechanism 36a wherein the switch 42a includes a stationary contact 46a mounted to the interior 26 of the first half segment 16 of the container 14. A moveable arm 48a is pivotly mounted at 50a to the interior 46 of the first half segment 16. A first spring 56 is disposed between the moveable arm 42a and the interior 26 of the first half segment 16 to bias the moveable arm 42a. A moveable contact 52a is mounted to other end of the second spring 54a to bias the moveable contact 52a towards the stationary contact 46a so that the moveable contact 52a will keep energizing the lamp 22 when the second half segment 16 is partially going into the open position so that a person (not shown) can view the lamp 22 to check that it is operating.

The magnetic member 40a of the magnetic fastener 34a shown in FIG. 3 is now an electromagnet in the electrical connection 30 and is still disposed onto the first half segment 16 of the container 14 so that when the segments are in the closed position the switch 42a will close and the electromagnet 40a will activate while making contact with the magnetizable member 38.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A device for sterilizing and storing toothbrushes which comprises:
    (a) a container having a first half segment and a second half segment hinged together so that in one instance said segments can be in an opened position and in another instance said segments can be in a closed position;
    (b) a lamp disposed within said first half segment for radiating ultraviolet rays;
    (c) a plurality of holders for supporting the toothbrushes, said holders spaced apart and affixed to interior of said first half segment and said second half segment;
    (d) reflecting surfaces on the interior of said first half segment for directing rays from said lamp over bristels of the toothbrushes;
    (e) an electrical connection from said lamp to a power source;
    (f) means for removably securing said first half segment to said second half segment in the closed position;
    (g) means for automatically deenergizing said lamp when said first half segment and said second half segment are in the opened position at a predetermined distance; wherein said removably securing means is a magnetic fastener comprising:
    (h) a magnetizable member affixed to said second half segment of said container;
    (i) a magnetic member affixed to said first half segment of said container so that when said segments are in the closed position said magnetic member and said magnetizable member will make contact with each other, wherein said automatically deenergizing means includes:
    (j) a switch in said electrical connection and disposed onto said first half segment of said container for controlling energization of said lamp;
    (k) an actuator attached to said second half segment of said container and controlled by movement thereof for operating said switch to energize said lamp when said second half segment is in the closed position and to deenergize said lamp when said second half segment is in the opened position, wherein said switch includes:
    (l) a stationary contact mounted to the interior of said first half segment of said container;
    (m) a moveable arm pivotly mounted to the interior of said first half segment;
    (n) a first spring disposed between said movable arm and the interior of said first half segment to bias said movable arm;
    (o) a second spring mounted at one end to said movable arm; and
    (p) a movable contact mounted to other end of said second spring to bias said movable contact towards said stationary contact so that said moveable contact will keep energizing said lamp when said second half segment is partially going into the open position so that a person can view said lamp to check that it is operating.

2. A device as recited in claim 1, wherein said magnetic member of said magnetic fastener is an electromagnet in said electrical connection and disposed onto said first half segment of said container so that when said segments are in the closed position said switch will close and said electromagnet will activate while making contact with said magnetizable member.

* * * * *